United States Patent
Aubriot et al.

[11] Patent Number: 5,326,358
[45] Date of Patent: Jul. 5, 1994

[54] KNEE JOINT PROSTHESIS

[75] Inventors: Jacques-Hubert Aubriot, Caen, France; Roland Willi, Neftenbach, Switzerland

[73] Assignee: Sulzer Medizinaltechnik AG, Winterthur, Switzerland

[21] Appl. No.: 937,220

[22] Filed: Aug. 27, 1992

[30] Foreign Application Priority Data

Aug. 28, 1991 [CN] China ................................. 2523/91

[51] Int. Cl.5 .................................................. A61F 2/38
[52] U.S. Cl. ............................................ 623/20; 623/18
[58] Field of Search ............... 623/16, 18, 19, 20, 623/22

[56] References Cited

U.S. PATENT DOCUMENTS

| 4,257,129 | 3/1981 | Volz | 623/20 |
| 4,568,348 | 2/1986 | Johnson et al. | 623/20 |
| 4,808,185 | 2/1989 | Penenberg | 623/20 |
| 5,116,376 | 5/1992 | May | 423/20 |
| 5,176,710 | 1/1993 | Hahn et al. | 623/20 |
| 5,201,881 | 4/1993 | Evans | 623/20 |

FOREIGN PATENT DOCUMENTS

| 0498586 | 8/1982 | European Pat. Off. | 623/20 |
| 3535112 | 4/1987 | Fed. Rep. of Germany | 623/20 |
| 2663536 | 12/1991 | France | 623/20 |
| 2120943 | 12/1983 | United Kingdom | 623/20 |

Primary Examiner—David Isabella
Attorney, Agent, or Firm—Townsend and Townsend Khourie and Crew

[57] ABSTRACT

A knee joint prosthesis includes two guide faces for receiving the condyles of a distal femur. The prosthesis includes a tibial plateau of polyethylene which is embedded in a metal tibial shank with a plate. The underside of the plate is planar and bears against a resection area of the tibia shaped as a planar endface. On the inside of the plate, in the region of the guide faces, pockets are formed. The pockets follow the curvature of the guide faces in sagittal planes and exhibit at their lowest point a maximum wall thickness of 1.5 mm, while the minimum wall thickness of the tibial plateau resting in the pockets amounts to 6.5 mm.

6 Claims, 1 Drawing Sheet

KNEE JOINT PROSTHESIS

BACKGROUND OF THE INVENTION

The invention relates to a knee joint prosthesis generally. More particularly, the invention relates to a prosthesis having a tibial plateau which is embedded by a plate in a metal tibial shank and exhibits two guide faces for the condyles of the distal femur, while the plate bears in the direction of the axis of the shank against a prepared endface of the tibia.

U.S. Pat. No. 4,568,348 discloses a knee joint prosthesis having a conical plate and a conical underpart of the tibial plateau. One problem of knee joint prostheses of that kind is that a relatively large amount of sound bone material must be removed in order to insert the prosthesis. Moreover conical anchoring areas which do not have axial symmetry are difficult to produce so that they are accurate in shape and stand at the correct height and angular position to the longitudinal axis of the tibia.

SUMMARY OF THE INVENTION

The present invention is directed to a prosthesis that results in little loss of supporting bone material. In accordance with the present invention, the underside of the prosthetic plate is planar and bears against a resection area shaped as a planar endface, and because the inside of the plate in the region of the guide faces contains pockets which follow the curvature of the guide faces in sagittal planes and exhibit at their lowest point a wall thickness of a maximum of 1.5 mm in the resection area, while the minimum wall thickness of the tibial plateau resting in the pockets amounts to 6.5 mm in the region of the pockets.

An advantage of the present invention is that a minimum distance is maintained between the guide areas for the condyles and the resection plane, which leaves sufficient bone material for optimum bearing and for a later revision prosthesis.

DESCRIPTION OF THE PREFERRED EMBODIMENT

Figure 2:
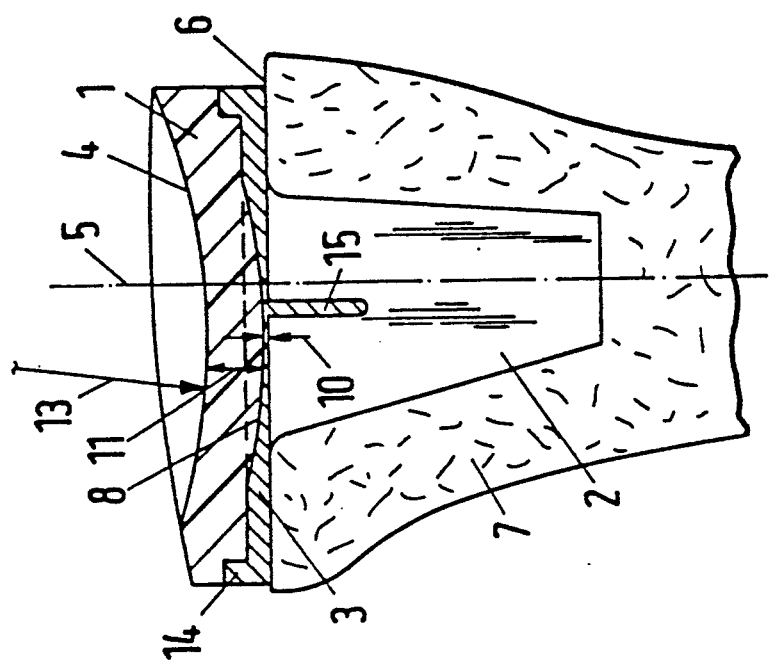
FIG. 2 is a vertical section of the knee joint prosthesis of FIG. 1 inserted in the tibia.

Referring to the drawings in detail wherein like numerals indicate like elements, a knee joint prosthesis is shown in accordance with the present invention. The prosthesis includes two guide faces or depressions 4 for the condyles of a distal femur. The prosthesis includes tibial plateau 1 of polyethylene which is embedded in a metal tibial shank 2 by plate 3. The underside of the plate is planar and bears against a resection area of the tibia 7. This resection area forms planar end face 6. On the inside of plate 3 in the region of the guide faces 4, are pockets or depressions 8, 9. Pockets 8, 9, following in sagittal planes the curvature of the guide faces 4, have, at their lowest point, a maximum wall thickness 10 of 1.5 mm, while the minimum wall thickness of the tibial plateau 1 resting in the pockets 8, 9 is 6.5 mm.

Figure 1:
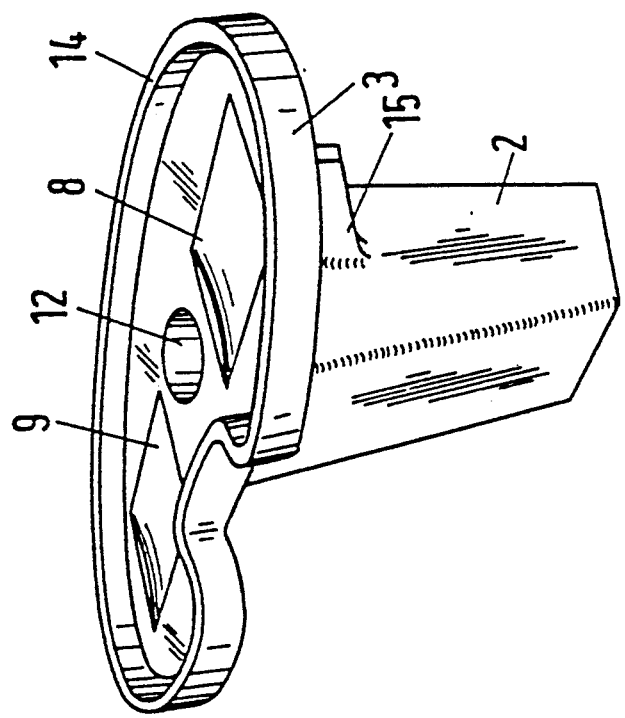
FIG. 1 is a perspective view of the tibial shank with the receiver areas for a tibial plateau in accordance with the present invention.

Referring to FIG. 1, planar plate 3 is molded onto shank 2 and is configured to bear against planar resection area 6 (FIG. 2). The conically tapering shank 2 has a rectangular cross-section in order to transmit torques positively. Strengthening ribs 15, which run parallel with the axis 5 of the shank, can likewise transmit torques in the axis of the shank and, in addition, strengthen the transition from the shank to the plate. Plate 3 is surrounded by an edge or rim 14 into which tibial plateau 1 is laid with a close fit. Pockets 8, 9 are formed on the inside of the plate, and lie underneath the condyle guide faces 4. The wall thickness 10 between the lowest point of the pockets 8, 9 and the endface 6 amounts to a maximum of 1.5 mm in order to be able to place the resection area as high as possible on the tibia. On the other hand, in accordance with FIG. 2, in the loading region of the tibial plateau a minimum wall thickness 11 of 6.5 mm for the polyethylene material is necessary in order to obtain guide faces of permanent shape. The pockets 8, 9 follow the curvature of guide faces 4 in sagittal planes so that an approximately constant wall thickness for tibial plateau 1 occurs over a greater angular range. In this way, forces in the joint which do not lie exactly along the axis 5 of the shank are transmitted within this angular range as normal forces between tibial plateau 1 and plate 3. This presupposes that tibial plateau 1 is resting in the pockets 8, 9. Shifting of forces of this kind result if the condyles rest against guide faces having a smaller radius than the radius 13 of guide faces 4. Upon insertion, tibial shank 2 is connected for primary anchoring, for example, via a drilled fastening hole 12, to an anchoring shank which is not shown.

We claim:

1. A knee joint prosthesis comprising a polyethylene tibial plateau having an upper and bottom surface, a plate having an upper and bottom surface, and a metal shank having a longitudinal axis, said bottom surface of the tibial plateau being coupled to said upper surface of the plate and said plate being secured to said metal shank and arranged to bear thereagainst along said longitudinal axis, said upper surface of the tibial plateau having two curved depressions contoured for receiving the femoral condyles of a distal femur, said bottom surface of the plate being planar for bearing against a tibia having a planar resection area, said upper surface of the plate having curved pockets beneath said depressions, the curvature of said pockets complementing in sagittal planes the curvature of said depressions, said plate, at the deepest point of said pockets, having a maximum wall thickness of 1.5 mm, and the thickness of said tibial plateau between said upper and bottom surface and above said pockets being a minimum of 6.5 mm.

2. The prosthesis of claim 1 further including a strengthening rib extending downwardly from said bottom surface of the plate beneath the deepest point of one of said pockets, said rib also extending in a lateral direction relative to said shank.

3. The prosthesis of claim 1 wherein the wall thickness of said tibial plateau along said depressions is substantially constant.

4. A knee joint prosthesis comprising:
a first member having top and bottom surfaces, said top surface having depressions formed therein for supporting the femoral condyles of a distal femur;
a second member having a top surface and a bottom surface, said second member top surface having depressions formed therein, said second member depressions complementing in sagittal planes said first member depressions, said second member bottom surface being essentially entirely planar for bearing against a planar tibial resection; and a shank extending from said second member.

5. The prosthesis of claim 4 wherein said second member, at the deepest point of said second member depressions, has a maximum wall thickness of 1.5 mm, and the thickness of said first member between said upper and bottom surface and above said first member depressions is a minimum of 6.5 mm.

6. A knee joint prosthesis comprising:

a polyethylene tibial plateau having an upper and bottom surface, the upper surface of the tibial plateau having two depressions contoured for receiving the femoral condyles of a distal femur;

a metal shank having a longitudinal axis; and a plate secured to the metal shank and arranged to bear thereagainst along said longitudinal axis, the plate having an upper and bottom surface, the upper surface of the plate being coupled to the bottom surface of the tibial plateau, the bottom surface of the plate being essentially planar for bearing against a tibia having an essentially planar resection area, the bottom surface of the plateau, at the deepest point of the depressions, being a maximum of 1.5 mm from the bottom surface of the plate.

* * * * *